(12) United States Patent
Mishkin et al.

(10) Patent No.: US 6,488,936 B1
(45) Date of Patent: **\*Dec. 3, 2002**

(54) IMMUNOGENIC COMPOSITION OF INTERLEUKIN-12 (IL-12), ALUM, HERPES SIMPLEX VIRAL (HSV) ANTIGEN, AND METHOD THEREOF

(75) Inventors: Eric M. Mishkin, Monroe, NY (US); John H. Eldridge, Fairport, NY (US)

(73) Assignee: Wyeth, Madison, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/247,635

(22) Filed: Feb. 10, 1999

Related U.S. Application Data
(60) Provisional application No. 60/074,503, filed on Feb. 12, 1998.

(51) Int. Cl.[7] .................. A61K 39/245; A61K 45/00
(52) U.S. Cl. ................... 424/229.1; 424/278.1; 424/204.1; 424/231.1; 536/23.72
(58) Field of Search ................... 424/229.1, 204.1, 424/231.1, 278.1; 530/351; 536/23.72

(56) References Cited

FOREIGN PATENT DOCUMENTS

WO     WO96/03510 A   *   2/1996

OTHER PUBLICATIONS

Biron et al. Curr. Opin. Immunol., 1995, vol. 7, No. 4, pp. 485–496, Aug. 1995.*
Baca–Estrada. Vaccine, 1997, vol. 15, No. 16, pp. 1753–1760.*
Mishkin et al. Vaccine, 1991, vol. 9, pp. 147–153.*
Ghiasi et al. Journal of Virology, vol. 68, pp. 2118–2126, Apr. 1994.*

* cited by examiner

*Primary Examiner*—Ali R. Salimi
(74) *Attorney, Agent, or Firm*—Alan M. Gordon

(57) ABSTRACT

This invention pertains to vaccine compositions comprising a mixture of antigen, such as a herpes simplex virus antigen, and the interleukin IL-12, which may be adsorbed onto a mineral in suspension. These vaccine compositions modulate the protective immune response to the antigen.

10 Claims, No Drawings

IMMUNOGENIC COMPOSITION OF INTERLEUKIN-12 (IL-12), ALUM, HERPES SIMPLEX VIRAL (HSV) ANTIGEN, AND METHOD THEREOF

This application claims priority from U.S. provisional application Serial No. 60/074,503, filed Feb. 12, 1998.

BACKGROUND OF THE INVENTION

The immune system uses many mechanisms for attacking pathogens; however, not all of these mechanisms are necessarily activated after immunization. Protective immunity induced by vaccination is dependent on the capacity of the vaccine to elicit the appropriate immune response to resist or eliminate the pathogen. Depending on the pathogen, this may require a cell-mediated and/or humoral immune response.

The current paradigm for the role of helper T cells in the immune response is that T cells can be separated into subsets on the basis of the cytokines they produce, and that the distinct cytokine profile observed in these cells determines their function. This T cell model Includes two major subsets: TH-1 cells that produce IL-2 and interferon γ (IFN-γ) which augment both cellular and humoral immune responses, and TH-2 cells that produce IL-4, IL-5 and IL-10 which augment humoral immune responses (Mosmann et al., *J. Immunol.* 126:2348 (1986)). It is often desirable to enhance the immunogenic potency of an antigen in order to obtain a stronger immune response in the organism being immunized and to strengthen host resistance to the antigen-bearing agent. A substance that enhances the immunogenicity of an antigen with which it is administered is known as an adjuvant. For example, certain lymphokines have been shown to have adjuvant activity, thereby enhancing the immune response to an antigen (Nencioni et al., *J. Immunol.* 139:800–804 (1987); EP285441 to Howard et al.).

SUMMARY OF THE INVENTION

This invention pertains to vaccine compositions comprising a mixture of herpes simplex virus glycoprotein D, the interleukin IL-12 and a mineral in suspension. The IL-12 may be either adsorbed onto the mineral suspension or simply mixed therewith. In a particular embodiment of the invention, the IL-12 is adsorbed onto a mineral suspension such as alum (e.g., aluminum hydroxide or aluminum phosphate). In a particular embodiment, the IL-12 is human IL-12. The invention also pertains to vaccine compositions which further comprise a physiologically acceptable vehicle. The invention further relates to immunogenic compositions comprising a mixture of a herpes simplex virus glycoprotein D, an adjuvant amount of interleukin-12, a mineral in suspension, and optionally comprising a physiologically acceptable vehicle.

The compositions of the present invention modulate the protective immune response to the antigen; that is, the vaccine composition is capable of quantitatively and qualitatively improving the vaccinated host's antibody response, and quantitatively increasing cell-mediated immunity for a protective response to a pathogen. In a particular embodiment of the invention, the antigen is a herpes simplex viral (HSV) antigen, such as envelope glycoprotein D (gD) of herpes simplex virus types I and/or II.

The invention also pertains to methods for preparing a vaccine composition comprising mixing HSV gD and IL-12 with a mineral in suspension. In particular, the IL-12 is adsorbed onto the mineral suspension. The invention also pertains to methods for eliciting or increasing a vaccinate's humoral and/or cell-mediated immunity, for a protective immune response, comprising administering to a vertebrate host an effective amount of a vaccine composition comprising a mixture of HSV gD, IL-12 and a mineral in suspension in a physiologically acceptable solution. In particular, the IL-12 is adsorbed onto the mineral suspension.

DETAILED DESCRIPTION OF THE INVENTION

Glycoprotein D (gD) is an envelope glycoprotein of herpes simplex virus (HSV) types I and II. HSV gD has been shown to be a potent inducer of protective immunity against primary and recurrent HSV infection in animal models (Mishkin et al., *Vaccine* 9:147–153 (1991); Landolfi et al., *Vaccine* 11:407–414 (1993)).

IL-12 is produced by a variety of antigen-presenting cells, principally macrophages and monocytes. It is a critical element in the induction of TH-1 cells from naive T cells. Production of IL-12 or the ability to respond to it has been shown to be critical in the development of protective TH-1-like responses, for example, during parasitic infections, most notably Leishmaniasis (Scott et al., U.S. Pat. No. 5,571, 515). The effects of IL-12 are mediated by IFN-γ produced by NK cells and T helper cells. IFN-γ is critical for the induction of IgG2a antibodies to T-dependent protein antigens (Finkelman and Holmes, *Annu. Rev. Immunol.* 8:303–33 (1990)) and IgG3 responses to T-independent antigens (Snapper et al., *J. Exp. Med.* 175:1367–1371 (1992)). Interleukin-12 (IL-12), originally called natural killer cell stimulatory factor, is a heterodimeric cytokine (Kobayashi et al., *J. Exp. Med.* 170:827 (1989)). The expression and isolation of IL-12 protein in recombinant host cells is described in International Patent Application WO 90/05147, published May 17, 1990.

The studies described herein relate to the utility of IL-12 as an adjuvant in a herpes simplex virus (HSV) vaccine. Accordingly, this invention pertains to vaccine compositions comprising a mixture of HSV gD, IL-12 and a mineral in suspension. In a particular embodiment of the invention, the IL-12 is adsorbed onto a mineral suspension such as alum (e.g., aluminum hydroxide or aluminum phosphate). These vaccine compositions modulate the protective immune response to HSV; that is, the vaccine composition is capable of eliciting the vaccinated host's cell-mediated immunity for a protective response to the pathogenic antigen.

IL-12 can be obtained from several suitable sources. It can be produced by recombinant DNA methodology; for example, the gene encoding human IL-12 has been cloned and expressed in host systems, permitting the production of large quantities of pure human IL-12. Also useful in the present invention are biologically active subunits or fragments of IL-12. Further, certain T lymphocyte lines produce high levels of IL-12, thus providing a readily available source. Commercial sources of recombinant human and murine IL-12 include Genetics Institute, Inc. (Cambridge, Mass.).

The antigen of this invention, e.g., an HSV antigen, can be used to elicit an immune response to she antigen in a vertebrate such as a mammalian host. For example, the antigen can be an HSV gD protein antigen or a portion thereof which retains the ability to stimulate an immune response.

The method of the present invention comprises administering to a mammal, particularly a human or other primate, an immunologically effective dose of a vaccine composition comprising a mixture of an antigen, e.g., an HSV gD antigen, an adjuvant amount of IL-12 and a mineral in suspension. In particular, the IL-12 is adsorbed onto the mineral suspension. As used herein, an "adjuvant amount" of IL-12 is intended to mean doses of from about 1 nanogram to about 20 micrograms, and more particularly from about 100 nanograms to about 5 micrograms. As used herein, an "immunologically effective" dose of the vaccine composition is a dose which is suitable to elicit an immune response. The particular dosage will depend upon the age, weight and medical condition of the mammal to be treated, as well as on the method of administration. Suitable doses will be readily determined by the skilled artisan. The vaccine composition can be optionally administered in a pharmaceutically or physiologically acceptable vehicle, such as physiological or phosphate buffered saline or ethanol polyols such as glycerol or propylene glycol. A small amount of detergent may also be included to enhance vaccine stability.

The vaccine composition may optionally comprise additional adjuvants such as vegetable oils or emulsions thereof, surface active substances, e.g., hexadecylamin, octadecyl amino acid esters, octadecylamine, lysolecithin, dimethyl-dioctadecylammonium bromide, N,N-dicoctadecyl-N'-N'bis (2-hydroxyethyl-propane diamine), methoxyhexadecylglycerol, and pluronic polyols; polyamines, e.g., pyran, dextransulfate, poly IC, carbopol; peptides, e g., muramly. dipeptide, dimethylglycine, tuftsin; immune stimulating complexes; oil emulsions; lipopolysaccharides such as MPL (3-O-deacylated monophosphoryl lipid A; RIBI ImmunoChem Research, Inc., Hamilton, Mont.); and mineral gels. The antigens of this invention can also be incorporated into liposomes, cochleates, biodegradable polymers such as poly-lactide, poly-glycolide and poly-lactide-co-glycolides, or ISCOMS (immunostimulating complexes), and supplementary active ingredients may also be employed. Antigens of the present invention can also be administered in combination with bacterial toxins and their attenuated derivatives. The antigens of the invention can also be administered in combination with other lymphokines including, but not limited to, interleukin-2, IFN-γ and GM-CSF.

The vaccines can be administered to a human or animal by a variety of routes, including but not limited to parenteral, intraarterial, intradermal, transdermal (such as by the use of slow release polymers), intramuscular, intraperitoneal, intravenous, subcutaneous, oral and intranasal routes of administration. The amount of antigen employed in such vaccines will vary depending upon the identity of the antigen. Adjustment and manipulation of established dosage ranges used with traditional carrier antigens for adaptation to the present vaccine is well within the ability of those skilled in the art. The vaccines of the present invention are intended for use in the treatment of both immature and adult warm-blooded animals, and, in particular, humans. Typically, the antigen and IL-12/alum combination will be administered at the same time.

The adjuvant action of IL-12 has a number of important implications. The adjuvanticity of IL-12 can increase the concentration of protective antibodies produced against the antigen in the vaccinated organism. As a result, effective (i.e., protective) vaccination can be achieved with a smaller quantity of antigen than would be normally required. This reduction in the required amount of antigen may lead to more widespread use of vaccines which are difficult and costly to prepare. Additionally, the use of IL-12 as an adjuvant can enhance the ability of antigens which are weakly antigenic or poorly immunogenic to elicit an immune response. It may also provide for safer vaccination when the antigen is toxic at the concentration normally required for effective immunization. By reducing the amount of antigen, the risk of toxic reaction is reduced.

Typically, vaccination regimens call for the administration of antigen over a period of weeks or months in order to stimulate a "protective" immune response. A protective immune response is an immune response sufficient to protect the immunized organism from disease caused by a particular pathogen or pathogens to which the vaccine is directed. IL-12, when administered with an antigen, such as an HSV antigen, and mixed with or adsorbed onto a mineral (e.g., alum) in suspension can accelerate the generation of a protective immune response. This may reduce the time course of effective vaccination regimens. In some instances, it may result in the generation of a protective response in a single dose. The vaccine compositions of this invention are also useful therapeutically, to reduce the number and severity of symptomatic episodes in subjects already infected with HSV.

As the result of work described herein, coadministration of HSV subunit vaccine with IL-12 adsorbed on alum in suspension has been shown to elicit an overwhelmingly TH-1-associated profile of response; this is a novel pattern of immune induction for gD subunit vaccine. As further described herein, dose ranges of TL-12 operative in preclinical models of immunization with soluble and aluminum phosphate adsorbed gD have been determined Results described herein also reveal that immunization with the cytokine/glycoprotein combination with or without alum elicits a TH-1-associated antibody profile. Coadministration of vaccine and IL-12/alum has adjuvant effects on immune responsiveness to the subunit vaccine as indicated by increases in the level of anti-gD antibodies measured by ELISA and virus neutralization.

Glycoprotein D (gD), an envelope glycoprotein of herpes simplex virus types I and II shown to be requisite for virus infectivity and a major target of humoral and cellular immune responses, serves as a primary vaccine candidate for use against primary and recurrent herpes infection in humans. Administration of gD subunit vaccine formulated with aluminum-based or other immunoadsorbents currently accepted for use in humans has been shown in several preclinical studies to induce a profile of immune response attributable to a predominant stimulation of TH-2 T helper lymphocytes. However, it appears that interdiction of recurrent herpes disease and the establishment of appropriate protective immune function will require the induction of a potent TH-1 profile of response.

Results of work described herein indicate that coadministration of IL-12 with soluble and $AlPO_4$-adsorbed gD results in a quantitative increase in humoral and cellular immune responses, as well as in a Qualitative alteration in the humoral response. This is demonstrated by the altered IgG subclass profile elicited by the vaccine in the presence of IL-12. Indeed, the preferential induction of IgG2a antibodies, with their efficient complement fixing capability, is one of the hallmarks of a TH-1 response profile. The immunomodulation of the immune response by IL-12 administration is also evident in the shifted proportion and magnitude of IFN-γ (TH-1 associated) secretion when compared with IL-4 (TH-2 associated).

Furthermore, it is particularly important to note the induction of antigen-specific cytolytic activity in mice immunized with soluble subunit vaccine coadministered with IL-12. This pattern of response suggests that the addition of IL-12 results in a fundamental change in the character of the immune response to gD subunit vaccines, because gD subunit vaccines have rarely, if ever, demonstrated the ability to induce cytolytic activity in previous studies.

The spectrum of immune response elicited by this novel formulation is closely correlated with that induced by natural virus infection and associated with a pattern of immunity observed in disease free seropositive humans. Taken together, these results suggest that IL-12-mediated immunomodulation provides a significant benefit in establishing an immunological response profile effective in immunotherapeutic and/or prophylactic intervention against herpes simplex virus disease.

The following Examples are offered for the purpose of illustrating the present invention and are not to be construed to limit the scope of this invention. The teachings of all references cited herein are hereby incorporated herein by reference.

EXAMPLES

Materials and Methods
Expression and Purification of Herpes Simplex Virus Glycoprotein D and Vaccine Preparation Preparation of herpes simplex virus glycoprotein D (gD) vaccine was as previously described in Landolfi et al. (*Vaccine* 11(4):407–414 (1993)).

Experimental Design

Female Balb/C mice were randomized into the groups outlined in Table 1 (N=10/group). On days 0 and 21, the animals received inocula of gD vaccine described above, alone or mixed with various doses of IL-12, intramuscularly in the thigh. Mice were individually bled prior to immunization and on 7-day intervals thereafter. Five mice from each group were sacrificed on days 28 and 35 to harvest immune spleen cells and vaginal washings. Analysis of serum and vaginal washes included quantitation of IgA and IgG subclass antibody responses to gD antigen by enzyme-linked immunoassay (EIA). Functional antibody activity was assessed by the capacity of sera to neutralize HSV infectivity. Cell-mediated activities were evaluated by cytolytic T lymphocyte assay, lymphoproliferation analysis and cytokine secretion patterns.

EIA Analysis

HSV gD-specific antibody responses of individual sera were quantified by EIA as described by York et al. (Vaccine 13:1706–1712 (1995)).

Briefly, 96-well plates were coated for 1 hour with purified gD at a concentration of 20 ng/well. The plates were washed three times with 0.01 M PBS and 0.1% Tween-20, then blocked using a solution of PBS and 1 BSA. Plates were incubated for 1 hour at room temperature, and then washed three times with 0.01 M PBS and 0.1% Tween-20. Serial two-fold dilutions of sera in 0.05 M Tris-buffered saline were then added to duplicate wells and incubated for 1 hour. Wells were washed with 0.01 M PBS and 0.1% Tween-20 prior to addition of secondary antibody. These antibodies consisted of horseradish peroxidase (HRP)-labeled goat anti-mouse IgG (1:2000 dilution in TBS and 0.1% Tween-20), and biotinylated goat anti-mouse IgG1 and IgG2a (400 ng/ml in TBS and 0.1% Tween-20). Avidin-HRP at a concentration of 50 ng/ml was added to the IgG1 and IgG2a detection wells. Following a 1 hour incubation, wells were washed prior to the addition of ABTS (2,2'-Azinobis(3-ethylbenzothiazoline)-6 sulfonic acid diammonium salt) substrate. Resulting color was quantitated at 405 nm for OD, and the titers determined by endpoint extrapolation.

Serum Neutralization

Individual sera were evaluated for HSV neutralizing titer using a microneutralization assay method as previously described (Mishkin et al., *Vaccine* 9:147–153 (1991)).

Briefly, Vero cells were grown to confluence in 96-well flat-bottomed plates. Test sera were heat inactivated for 30 minutes at 56° C. and then subjected to serial 2-fold dilution in medium to yield 0.1 ml volumes. An equal volume of HSV1 or HSV2 (containing approximately 100 pfu of virus) was then added. For complement-dependent assays, 10% (v/v) guinea pig complement was also included. Virus/serum/(complement) mixtures were then incubated for 1 hour at 37° C. (5% $CO_2$) with gentle rocking, prior to addition directly onto Vero cell monolayers. Virus (i.e., medium without serum), medium (i.e., uninfected cells), and complement (i.e., medium without serum or complement) controls were included in each assay. Following incubation at 37° C., the cells were overlaid with 1% methylcellulose. Plates were incubated at 37° C. (5% $CO_2$) until approximately 50 plaques could be counted in virus control wells (i.e., 48–72 hours). Plaques were enumerated, and titers were defined as the reciprocal of the last serum dilution yielding greater than 50% plaque reduction.

Lymphoproliferative Response

Methods for the assay of HSV-specific lymphoproliferation have previously been described in detail (Ishizaka et al., *Viral Immunology* 4:187–193 (1991)). Spleen cells were harvested from mice and pooled in supplemented RPMI (Roswell Park Memorial Institute medium Number 1640, a common tissue culture medium used in lymphocyte culture systems). Cells were then plated at $2 \times 10^5$ viable cells/well in 96-well flat-bottomed plates in 0.1 ml. Five replicate wells were included for each in vitro stimulating antigen used. These included medium, Vero cell lysate, HSV1 ($10^5$ heat inactivated pfu/well) HSV2 ($10^5$ heat inactivated pfu/well) and purified baculovirus-expressed recombinant glycoprotein D of HSV2 (bgD2) (20 ng/well). These were each delivered in 0.1 ml volumes Plates were then incubated for 5 days at 37° C. (5% CO). Five to six hours prior to harvest, each well was pulsed with 0.5 µCi of $^3$H-thymidine in 25 ml of RPMI. Cells were harvested onto glass fiber filter mats using a cell harvester, and incorporated activity was determined using a Betaplate counter.

Cytotoxic T Cell Activity

As previously described (York et al., 1995) spleen cells were used in a secondary stimulation of specific CTL activity. In the present experiments, spleen cells were harvested 14 weeks post-immunization. Spleen cell suspensions were prepared and then treated with 0.17% $NH_4Cl$ (5 ml/spleen) for 4 minutes at RT to osmotically remove erythrocytes. Cells were then washed, counted and tested for viability by Trypan blue dye exclusion.

Spleen cells from naive animals were used as antigen presenting cells (APC). These were subjected to γ-irradiation (2000R) and were then infected with HSV1 (strain NS) and HSV2 (strain 186) at a multiplicity of infection (MOI) of 5 for 1 hour at 37° C. (5% $CO_2$) with swirling. Cells were washed once, resuspended at $5 \times 10^6$ cells/ml and allowed to incubate for another 4 hours. Virus was then inactivated by exposure to short-wave UV irradiation or 15 minutes. APC were added (1 ml containing $5 \times 10^6$ cells) to $2 \times 10^7$ effector cells/well in 5 ml of medium. Cultures were then incubated for 5 days prior to $^{51}$Cr-release assay for cytolytic activity.

Effector cells were harvested from plates following in vitro restimulation and assessed for viability using Trypan blue exclusion. Cell concentrations were then adjusted in medium and plated in triplicate aliquots of 200 μl to yield the desired effector:target (E:T) ratio. Doubling dilutions mere then performed.

A20 target cells were harvested in appropriate numbers for assay. These were infected with HSV1 and HSV2 at a MOI of 10 for an initial 1 hour absorption period, washed and incubated for an additional 3 hours. Uninfected A20 cells, to be used as controls, were mock-infected in an identical manner. Following the 3 hour incubation period, $5 \times 10^6$ to $1 \times 10^7$ A20 targets were pelleted and resuspended in 0.2 ml of fetal calf serum, to which was added 200 μCi of $^{51}$Cr, and incubated for 1 hour (37° C., 5% $CO_2$). Cells were then washed twice in 10 ml of RPMI, resuspended in 1 ml of medium, and diluted to yield 100 ml aliquots at the appropriate E:T ratios.

Effector and labeled target cells were incubated (37° C., 5% $CO_2$) for 4 hours, at which time 100 μl of supernatant from each well was carefully collected and assessed for gamma emissions on a gamma counter. Total release was determined using triplicate wells of labeled targets treated with 2% Tween-20. Spontaneous release was enumerated from triplicate wells of labeled target cells incubated for 4 hours in medium only. Percent specific release was calculated using the following formula:

N Specific release=

$$\% \text{ Specific release} = \frac{(CPM_{experimental}) - (CPM_{spontaneous})}{(CPM_{total}) - (CPM_{spontaneous})} \times 100$$

Cytokine Analysis

As previously reported (York et al., 1995), the enzyme-linked immunospot assay (ELISPOT) was used for the direct enumeration of cells secreting IL-4 and IFN-γ. Under sterile conditions, Mill-pore HA nitrocellulose 96-well millititer plates were coated with 100 μl volumes of anti-cytokine MoAb at a concentration of 5 μg/ml (anti-IFN-γ) or 2 μg/ml (anti-IL-4) in sterile PBS. Plates were incubated overnight at room temperature and then washed 4 times with sterile water and then 3 times with PBS and 0.05% Tween-20. Wells then were blocked using 0.2 ml of RPMI 1640 and 1% BSA and incubated in 5% $CO_2$ (37° C.) for 10 minutes. During this time, cell suspensions of desired concentrations were prepared.

The blocking solution was removed by washing 3 times each with PBS and with PBS containing 0.05% Tween-20. Cells, at predetermined concentrations and dilutions (i.e., $1 \times 10^6$/well), were inoculated in triplicate into wells at a 0.1 ml volume. Plates were incubated for 20 hours in a 5% $CO_2$ (37° C.) incubator. Cells were removed by washing 3 times each with PBS followed by PBS and 0.05% Tween-20. Biotinylated MoAb was then prepared in PBS and 0.05% Tween-20+1% FBS at a final concentration of 0.25 μg anti-IFN-γ/ml or 4 μg anti-IL-4/ml, and 0.1 ml of the antibody solution added to the wells. Plates were incubated overnight at 4° C. in a humid chamber.

Spots were developed by washing the plates 3 times with PBS and 0.05% Tween-20 prior to the addition of 0.1 ml/well of peroxidase-conjugated goat anti-biotin antibody diluted 1:400 in PBS and 0.05% Tween-20 +1% FBS.

For visualization of spots, plates were washed 3 times with PBS prior to the addition of 0.2 ml of substrate. This was prepared by dissolving 10 mg 3-amino-9-ethylcarbazole to 1 ml of dimethylformamide in a glass tube followed by the addition of 30 ml of 0.1 M sodium acetate buffer. Just before use, 15 μl $H_2O_2$ was added to the substrate solution. Spots were developed for 5–15 minutes at room temperature, and development was stopped by the addition of tap water. Spots were enumerated using a dissecting microscope.

Results

EIA Responses

Anti-gD IgG class and subclass responses are summarized in Table 1. Titers of less than 50 (the first serum dilution) were assigned a titer of 25. On day 7, only mice primed with live HSV1 exhibited significant total IgG titers (Table 1a). However, a measurable level of activity was recorded for sera from animals receiving soluble gD and IL-12. By day 28, a pattern of augmented response was seen in mice receiving soluble subunit vaccine and IL-12 at all doses of cytokine when compared with soluble vaccine alone. Here, responses were maximum in sera from mice administered soluble gD with 1.0 μg IL-12. In mice receiving $AlPO_4$-adsorbed glycoprotein, enhanced IgG EIA responses were observed only in animals immunized with $AlPO_4$ and gD plus 0.2 μg IL-12, which resulted in an approximately two-fold increase. By day 35, a dose dependent IL-12 adjuvant effect was seen for the total IgG antibody response to soluble gD (no $AlPO_4$). Coadministration of 0.2, 1.0 and 5.0 μg of IL-12 with gD resulted in 5-, 24- and 215-fold increased responses, respectively. In contrast, when IL-12 was added to $AlPO_4$-adsorbed gD, maximum responsiveness occurred with 0.2 μg of IL-12.

IgG1 responses (Table 1b) were not observed on day 7 in any treatment group except HSV1-infected animals, in whom a low level of activity was seen. Titers of less than 50 (the first serum dilution) were assigned a titer of 25. By day 28, maximal IgG1 anti-gD responses were seen in sera from mice immunized with $AlPO_4$-adsorbed glycoprotein without IL-12. Indeed, addition of IL-12 to $AlPO_4$ adsorbed vaccine resulted in an overt and dose-related reduction in this response. In contrast, coadministration of IL-12 with soluble gD resulted in an enhanced IgG1 response in comparison with subunit alone. However, no IL-12 formulation yielded a level of activity as great as that observed for $AlPO_4$ adsorbed subunit alone. By day 35, IgG1 titers waned in all groups. At this time, IgG1 titers of mice receiving soluble gD with IL-12 had reached comparable levels to those seen following immunization with $AlPO_4$-adsorbed subunit vaccine.

IgG2a anti-gD responses (Table 1c) were evident by day 7 in HSV1-primed animals. Titers of less than 50 (the first serum dilution) were assigned a titer of 25. A modest response was also noted at this time with soluble gD which had been administered with 0.2 or 5.0 μg IL-12. On day 28, substantially increased IgG2a titers resulted from the administration of IL-12. This was particularly evident in animals receiving soluble gD, where greater than 1000-fold increases in titer were observed. Coadministration of IL-12 and $AlPO_4$ adsorbed vaccine also resulted in a significant increase in gD-specific IgG2a antibodies. In this case, IgG2a antibody responses were maximal when 0.2 μg IL-12 was used, suggesting that alum-bound IL-12 significantly enhanced biologic activity. On day 35, patterns of response noted for total IgG were closely paralleled by the IgG2a response and indicated that coadministration of IL-12 with subunit gD vaccine resulted in a significant adjuvant effect, as well as the elicitation of high titers of IgG2a antibody.

TABLE 1a

IL-12 Enhancement of the Plasma IgG Antibody Response to HSV-2 gD Immunization

| | Plasma IgG Anti-gD Titer | | | | | |
|---|---|---|---|---|---|---|
| Immunization | Day 7 | | Day 28 | | Day 35 | |
| Regimen | Mean | S.E. | Mean | S.E. | Mean | S.E. |
| gD | 25 | 0 | 29,159 | 10,420 | 9,063 | 2,993 |
| gD + 0.2 μg IL-12 | 63 | 21 | 146,651 | 39,157 | 49,813 | 15,456 |
| gD + 1.0 μg IL-12 | 34 | 7 | 210,267 | 67,806 | 217,061 | 88,404 |
| gD + 5.0 μg IL-12 | 71 | 36 | 131,628 | 51,401 | 1,949,697 | 1,845,964 |
| gD/AlPO$_4$ | 25 | 0 | 95,979 | 23,312 | 62,578 | 34,793 |
| gD/AlPO$_4$ + 0.2 μg IL-12 | 25 | 0 | 212,949 | 44,935 | 179,917 | 116,925 |
| gD/AlPO$_4$ + 1.0 μg IL-12 | 25 | 0 | 82,313 | 52,122 | 69,958 | 47,544 |
| gD/AlPO$_4$ + 5.0 μg IL-12 | 25 | 0 | 32,182 | 29,807 | 28,673 | 24,310 |
| AlPO$_4$ + 5.0 μg IL-12 | 25 | 0 | 25 | 0 | 25 | 0 |
| HSV1 (1 × 10$^6$ pfu) | 783 | 515 | 1,824 | 514 | 4,446 | 1,807 |

TABLE 1b

IL-12 Enhancement of the Plasma IgG1 Antibody Response to HSV-2 gD Immunization

| | Plasma IgG1 Anti-gD Titer | | | | | |
|---|---|---|---|---|---|---|
| Immunization | Day 7 | | Day 28 | | Day 35 | |
| Regimen | Mean | S.E. | Mean | S.E. | Mean | S.E. |
| gD | 25 | 0 | 14,323 | 4,939 | 4,421 | 1,019 |
| gD + 0.2 μg IL-12 | 25 | 0 | 40,246 | 13,626 | 22,464 | 4,427 |
| gD + 1.0 μg IL-12 | 25 | 0 | 59,536 | 25,196 | 21,592 | 5,511 |
| gD + 5.0 μg IL-12 | 25 | 0 | 17,637 | 8,137 | 5,512 | 3,023 |
| gD/AlPO$_4$ | 25 | 0 | 82,882 | 57,045 | 17,232 | 5,177 |
| gD/AlPO$_4$ + 0.2 μg IL-12 | 25 | 0 | 28,247 | 4,147 | 10,421 | 4,726 |
| gD/AlPO$_4$ + 1.0 μg IL-12 | 25 | 0 | 1,604 | 734 | 5,426 | 3,588 |
| gD/AlPO$_4$ + 5.0 μg IL-12 | 25 | 0 | 1,345 | 1,206 | 3,957 | 24,310 |
| AlPO$_4$ + 5.0 μg IL-12 | 25 | 0 | 25 | 0 | 25 | 0 |
| HSV1 (1 × 10$^6$ pfu) | 43 | 17 | 180 | 53 | 209 | 1,807 |

TABLE 1c

IL-12 Enhancement of the Plasma IgG2a Antibody Response to HSV-2 gD Immunization

| | Plasma IgG2a Anti-gD Titer | | | | | |
|---|---|---|---|---|---|---|
| Immunization | Day 7 | | Day 28 | | Day 35 | |
| Regimen | Mean | S.E. | Mean | S.E. | Mean | S.E. |
| gD | 25 | 0 | 25 | 0 | 152 | 127 |
| gD + 0.2 μg IL-12 | 32 | 7 | 36,807 | 12,926 | 6,009 | 1,846 |
| gD + 0.1 μg IL-12 | 25 | 0 | 49,034 | 18,983 | 33,547 | 11,290 |
| gD + 5.0 μg IL-12 | 36 | 11 | 39,943 | 22,448 | 67,681 | 53,732 |
| gD/AlPO$_4$ | 25 | 0 | 522 | 330 | 30 | 5 |
| gD/AlPO$_4$ + 0.2 μg IL-12 | 25 | 0 | 48,321 | 19,366 | 47,153 | 40,467 |
| gD/AlPO$_4$ + 1.0 μg IL-12 | 25 | 0 | 22,400 | 12,011 | 7,715 | 3,418 |
| gD/AlPO$_4$ + 5.0 μg IL-12 | 25 | 0 | 5,801 | 5,288 | 2,669 | 1,195 |
| AlPO$_4$ + 5.0 82 g IL-12 | 25 | 0 | 25 | 0 | 25 | 0 |
| HSV1 (1 × 10$^6$ pfu) | 746 | 603 | 659 | 227 | 668 | 283 |

Secretory Antibody Responses

Vaginal secretions were assayed for antibody activity following immunization with IL-12-formulated gD. IgA anti-gD (Table 2a) was observed in a number of treatment groups. Maximal titers occurred in the secretions derived from mice receiving soluble gD and 1.0 μg IL-12. This group also exhibited the highest titer of IgG anti-gD (Table 2b) on day 28. A relatively robust IgG titer was seen in mice administered AlPO$_4$ adsorbed gD with 0.2 μg IL-12. Titers of less than 5 (the first serum dilution) were assigned a titer of 3. On day 35, there was no significant gD-specific IgA in the vaginal wash fluids of any group. However, animals immunized with either soluble or AlPO$_4$-adsorbed gD plus 5.0 μg of IL-12 exhibited marked vaginal wash titers of antigen-specific IgG.

TABLE 2a

Mucosal IgA Anti-HSV-2 Responses to IL-12-Formulated gD

| | Vaginal Wash IgA Anti-gD Titer | | | |
|---|---|---|---|---|
| Immunization | Day 28 | | Day 35 | |
| Regimen | Mean | S.E. | Mean | S.E. |
| gD | 6.2 | 3.2 | 3.0 | 0 |
| gD + 0.2 μg IL-12 | 9.4 | 4.0 | 3.0 | 0 |
| gD + 1.0 μg IL-12 | 25.0 | 7.7 | 4.0 | 1.0 |
| gD + 5.0 μg IL-12 | 3.0 | 0 | 4.0 | 1.0 |
| gD/AlPO$_4$ | 9.8 | 6.8 | 3.2 | 0.2 |
| gD/AlPO$_4$ + 0.2 μg IL-12 | 3.0 | 0 | 3.0 | 0 |
| gD/AlPO$_4$ + 1.0 μg IL-12 | 3.0 | 0 | 3.0 | 0 |
| gD/AlPO$_4$ + 5.0 μg IL-12 | 3.0 | 0 | 3.0 | 0 |
| AlPO$_4$ + 5.0 μg IL-L2 | 6.2 | 3.2 | 3.0 | 0 |
| HSV1 (1 × 10$^6$ pfu) | 4.6 | 1.6 | 3.0 | 0 |

TABLE 2b

Mucosal IgG Anti-HSV-2 Responses to IL-12-Formulated gD

| Immunization Regimen | Vaginal Wash IgG Anti-gD Titer | | | |
|---|---|---|---|---|
| | Day 28 | | Day 35 | |
| | Mean | S.E. | Mean | S.E. |
| gD | 12.2 | 9.2 | 5.6 | 2.6 |
| gD + 0.2 µg IL-12 | 7.4 | 3.0 | 5.0 | 0.9 |
| gD + 1.0 µg IL-12 | 521.2 | 134.9 | 8.6 | 3.2 |
| gD + 5.0 µg IL-12 | 15.0 | 12.0 | 61.6 | 28.5 |
| gD/AlPO$_4$ | 13.2 | 3.6 | 18.6 | 3.4 |
| gD/AlPO$_4$ + 0.2 µg IL-12 | 165.41 | 143.1 | 3.0 | 0 |
| gD/AlPO$_4$ + 1.0 µg IL-12 | 12.2 | 9.2 | 3.0 | 0 |
| gD/AlPO$_4$ + 5.0 µg IL-12 | 50.8 | 6.2 | 123.4 | 59.0 |
| AlPO$_4$ + 5.0 µg IL-12 | 3.0 | 0 | 3.0 | 0 |
| HSV1 (1 × 10$^6$ pfu) | 3.0 | 0 | 3.0 | 0 |

Serum HSV-2 Neutralization Titers

Complement enhanced neutralizing antibody titers (Table 3) were increased in a dose-dependent manner the sera from mice receiving soluble gD with IL-12. These titers were increased by 5-, 15- and 50-fold at cytokine levels of 0.2, 1.0 and 5.0 µg, respectively. Titers of less than 10 (first serum dilution) were assigned a titer of 5. As in the case of the anti-gD responses measured by ELISA, the maximal virus neutralizing response induced by alum-adsorbed gD was induced with 0.2 µg IL-12.

TABLE 3

IL-12 Enhancement of the Plasma Neutralizing Antibody Response to gD Immunization

| Immunization Regimen | Plasma HSV-2 Neutralization Titer | |
|---|---|---|
| | Mean | S.E. |
| gD | 22.5 | 11.1 |
| gD + 0.2 µg IL-12 | 111.2 | 29.0 |
| gD + 1.0 µg IL-12 | 353.4 | 116.2 |
| gD + 5.0 µg IL-12 | 1,125.8 | 852.4 |
| gD/AlPO$_4$ | 81.0 | 40.9 |
| gD/AlPO$_4$ + 0.2 µg IL-12 | 294.8 | 213.7 |
| gD/AlPO$_4$ + 1.0 µg IL-12 | 17.9 | 7.0 |
| gD/AlPO$_4$ + 5.0 µg IL-12 | 8.5 | 2.2 |
| AlPO$_4$ + 5.0 µg IL-12 | 5.0 | 0 |
| HSV1 (1 × 10$^6$ pfu) | 100.8 | 52.2 |

Lymphoproliferative Responses

In vitro blastogenic responses to recall antigen are summarized in Table 4. A recall antigen is an antigen that the host has encountered previously; in the present case, the recall antigen for immunized mice is gD. The use of the term with respect to HSV-1 and HSV-2 assumes a high degree of crossreactivity with virus-expressed gD. No group was observed to demonstrate high levels of nonspecific activity to Vero cell control antigen. Heterologous responses to HSV-1 antigen were maximized in cells harvested from mice immunized with soluble and AlPO$_4$ adsorbed gD with 1.0 µg IL-12. Similar patterns of response were recorded for in vitro simulation with HSV2 and gD2 antigens. Interestingly, spleen cells from mice primed with HSV-1 demonstrated responsiveness to HSV-2 gD in the current experiment.

TABLE 4 gD/IL-12 Lymphoproliferative responses

| Immunization Regimen | Stimulation Indices to In Vitro Stimuli | | | |
|---|---|---|---|---|
| | Vero | HSV1 | HSV2 | gD2 |
| gD | 0.73 | 0.32 | 1.79 | 2.39 |
| gD + 0.2 µg IL-12 | 1.77 | 1.31 | 11.54 | 6.14 |
| gD + 1.0 µg IL-12 | 0.51 | 29.18 | 17.42 | 2.59 |
| gD + 5.0 µg IL-12 | 0.60 | 3.78 | 7.97 | 1.58 |
| gD/AlPO$_4$ | 1.08 | 0.67 | 4.19 | 5.87 |
| gD/AlPO$_4$ + 0.2 µg IL-12 | 1.13 | 4.44 | 3.14 | 1.67 |
| gD/AlPO$_4$ + 1.0 µg IL-12 | 0.68 | 16.54 | 33.87 | 17.79 |
| gD/AlPO$_4$ + 5.0 µg IL-12 | 1.25 | 4.2 | 4.42 | 1.71 |
| AlPO$_4$ + 5.0 µg IL-12 | 0.91 | 1.64 | 1.96 | 2.28 |
| HSV1 (1 × 10$^6$ pfu) | 0.94 | 2.71 | 9.15 | 1.36 |

Cytokine Responses

Cytokine profiles were assessed for selected groups of mice using a 1.0 µg dose of IL-12 and are summarized in Table 5. In comparison to administration of soluble or AlPO$_4$ adsorbed gD administered alone, addition of IL-12 resulted in significant increases in the secretion of IFN-γ relative to IL-4.

TABLE 5

Cytokine profiles

| Immunization Regimen | SFC/10$^6$ cultured cells | | |
|---|---|---|---|
| | IL-4 | IFN-γ | IFN-γ/IL-4 |
| 5 µg gD | 35 | 45 | 1.28 |
| 5 µg gD + 1 µg IL-12 | 85 | 215 | 2.53 |
| 5 µg gD/AlPO$_4$ | 40 | 35 | 0.88 |
| 5 µg gD/AlPO$_4$ + 1 µg IL-12 | 60 | 185 | 3.08 |
| AlPO$_4$ + 1 µg IL-12 | 50 | 85 | 1.70 |
| HSV1 | 495 | 545 | 1.10 |
| naive | 30 | 65 | 1.85 |

Cytolytic Activity

CTL responses for animals immunized with gD plus 1.0 µg of IL-12, or control vaccines are summarized in Table 6. HSV-1-primed mice yielded relatively uniform cytolytic activity at E:T ratios ranging from 25:1 to 3:1. Comparable levels of killing were observed in immunocyte cultures derived from mice immunized with soluble gD plus 1.0 µg IL-12. No significant cytolytic activity was seen in the spleen cells from any other vaccine or control group.

TABLE 6

CTL activity

| Immunization | Net Cytolysis at E:T Ratio | | | |
|---|---|---|---|---|
| | 25:1 | 12:1 | 6:1 | 3:1 |
| gD | 4.9 | −1.0 | 7.2 | 9.3 |
| gD + 1.0 µg IL-2 | 29.3 | 7.6 | 23.6 | 18.1 |
| gD/AlPO$_4$ | 10.1 | 7.6 | 9.7 | 3.1 |
| gD/lPO$_4$ + 1.0 µg IL-12 | 7.1 | 5.6 | 6.5 | 5.5 |
| AlPO$_4$ + 1.0 µg IL-12 | 15.1 | −3.4 | 2.4 | −4.7 |
| HSV1 | 24.6 | 36.9 | 32.1 | 26.1 |
| naive | −0.3 | 3.7 | — | 4.0 |

Equivalents

Those skilled in the art will recognize, or be able to ascertain, using no more than routine experimentation, many equivalents to the specific embodiments of the invention described herein. Such equivalents are intended to be encompassed in the scope of the invention.

What is claimed is:

1. An immunogenic composition comprising a mixture of a herpes simplex virus antigen, wherein the herpes simplex virus antigen is selected from the group consisting of glycoprotein D of herpes simplex type I, glycoprotein D of herpes simplex type II and combinations thereof, an adjuvant amount of interleukin-12 and an aqueous suspension of alum, and optionally comprising a physiologically acceptable vehicle.

2. An immunogenic composition according to claim 1, wherein the interleukin-12 is adsorbed onto the alum suspension.

3. An immunogenic composition according to claim 1, wherein the interleukin-12 is human interleukin-12.

4. An immunogenic composition according to claim 1, wherein the alum is aluminum hydroxide or aluminum phosphate.

5. An immunogenic composition according to claim 1, wherein the adjuvant amount of interleukin-12 is from about 1 nanogram to about 20 micrograms.

6. A method of eliciting an immune response to a herpes simplex virus antigen, comprising administering to a vertebrate host an effective amount of a composition comprising a mixture of a herpes simplex virus antigen, wherein the herpes simplex virus antigen is selected from the group consisting of glycoprotein D of herpes simplex type I, glycoprotein D of herpes simplex type II and combinations thereof, an adjuvant amount of interleukin-12 and an aqueous suspension of alum, and optionally comprising a physiologically acceptable vehicle.

7. A method according to claim 6, wherein the interleukin-12 is adsorbed onto the alum suspension.

8. A method according to claim 6, wherein the interleukin-12 is human interleukin-12.

9. A method according to claim 6, wherein the alum is aluminum hydroxide or aluminum phosphate.

10. A method according to claim 6, wherein the adjuvant amount or interleukin-12 is from about 1 nanogram to about 20 micrograms.

\* \* \* \* \*